United States Patent [19]

Linn et al.

[11] Patent Number: 4,797,273

[45] Date of Patent: Jan. 10, 1989

[54] SKIN MOISTURIZING MICROEMULSIONS

[75] Inventors: Edwards E. Linn, Wanaque, N.J.; Thomas O. York, Indianapolis, Ind.

[73] Assignee: Elizabeth Arden Inc., New York, N.Y.

[21] Appl. No.: 928,217

[22] Filed: Nov. 7, 1986

Related U.S. Application Data

[63] Continuation-in-part of Ser. No. 798,501, Nov. 15, 1985.

[51] Int. Cl.$^4$ .......................... A61K 7/42; A61K 7/44; A61K 7/48; A61K 9/10
[52] U.S. Cl. .................................... 424/59; 252/311; 424/60; 514/847; 514/937
[58] Field of Search ................... 424/59, 60; 514/847, 514/937

[56] References Cited

U.S. PATENT DOCUMENTS

| | | | |
|---|---|---|---|
| 3,392,040 | 7/1968 | Kass | 106/287 |
| 3,778,381 | 12/1973 | Rosano et al. | 252/311 |
| 3,917,830 | 11/1975 | Davis et al. | 424/243 |
| 4,052,331 | 10/1977 | Dumoulin | 252/312 |
| 4,146,499 | 3/1979 | Rosano | 252/186 |
| 4,254,104 | 3/1981 | Suzuki | 424/170 |
| 4,563,346 | 1/1986 | Deckner | 424/60 |
| 4,595,586 | 6/1986 | Flom | 424/60 |
| 4,597,963 | 7/1986 | Deckner et al. | 424/60 |
| 4,604,281 | 8/1986 | Deckner | 424/60 |
| 4,608,392 | 8/1986 | Jacquet | 424/60 |
| 4,663,155 | 5/1987 | Murray et al. | 424/60 |
| 4,663,156 | 5/1987 | Elum et al. | 424/60 |

FOREIGN PATENT DOCUMENTS

| | | | |
|---|---|---|---|
| 125779 | 11/1984 | European Pat. Off. | |
| 2509989 | 1/1983 | France | 424/60 |
| 2079300 | 1/1982 | United Kingdom | |
| 2098865 | 12/1982 | United Kingdom | 424/243 |
| 2113568 | 8/1983 | United Kingdom | |
| 2155337 | 9/1985 | United Kingdom | |

OTHER PUBLICATIONS

Jayakrishnan et al., "Microemulsions: Evolving Technology For Cosmetic Applications", *J. Soc. Cosmet. Chem.*, 34, 335–350 (1983).

*Emulsions and Emulsion Technology,* Part 1, Ed. Kenneth J. Lissant, Marcel Dekker, Inc., New York, Chapter 3, "Microemulsions" (1974).

*Microemulsions-Theory and Practice,* Ed. Leon M. Prince, Academic Press, Inc., New York, pp. 1–56, 149–179 (1977).

Chemical Abstracts, vol. 93, No. 18, p. 346, Abstract No. 173618f (Face Lotions).

*Primary Examiner*—Dale R. Ore
*Attorney, Agent, or Firm*—Kenyon & Kenyon

[57] ABSTRACT

The present invention provides water-in-oil microemulsions suitable for cosmetic uses containing moisturizing agents or sunscreens. Also disclosed are methods of moisturizing dry skin using water-in-oil or oil-in-water microemulsions containing moisturizing agents. Finally, methods of potentiating the effects of macroemulsion moisturizing creams and lotions by the prior application of water-in-oil and oil-in-water microemulsions are also provided.

57 Claims, No Drawings

SKIN MOISTURIZING MICROEMULSIONS

CROSS-REFERENCE TO RELATED APPLICATION

This application is a continuation-in-part of Ser. No. 798,501, filed Nov. 15, 1985.

BACKGROUND OF THE INVENTION

An emulsion is a dispersed system containing at least two immiscible liquid phases, one of which is dispersed in the form of small droplets throughout the other, and an emulsifying agent in order to improve the stability of the system.

There are two types of emulsions depending on the droplet size of the liquids present in the emulsions. Macroemulsions do not permit light to pass through them since the droplets have average diameters of about 10 to about 1000 microns. These emulsions typically appear milky white. Microemulsions are stable systems consisting of droplets which are significantly smaller, being approximately 0.2 microns, or smaller, in diameter on the average. As such, microemulsions are translucent, and routinely transparent, in appearance.

Microemulsions are an extraordinary type of emulsion that forms spontaneously. Products consisting of these systems are valued for their stability and small particle size, which affords microemulsions special consideration in the market place. Additional information on microemulsions and their properties may be obtained from *Emulsions and Emulsion Technology* Part I, ed. Kenneth J. Lissant, Marcel Dekker, Inc., New York, Chapter 3 "Microemulsions"(1974) and *Microemulsions Theory and Practice* ed. Leon M. Prince, Academic Press, Inc. (1977).

Emulsions have a variety of uses, most notably as vehicles for the delivery of medicines. In particular, microemulsions are known to deliver pharmacologically active agents as disclosed in U.K. Patent No. 2,098,865. Microemulsions are also known to provide injectable compositions containing an anaesthetic, as disclosed in U.S. Pat. No. 3,917,830, and are known as carriers for oxygen absorbing fluorinated organic compounds, as disclosed in U.S. Pat. No. 3,778,381. Jayakrishnan et al. in *J. Soc. Cosmet. Chem.* 34, 335–350 (1983) disclose the delivery of hydrocortisone with microemulsions. Finally, U.S. Pat. No. 4,146,499 discloses oil-in-water microemulsions allegedly capable of containing a variety of hydrophobic substances including certain cosmetics.

SUMMARY OF THE INVENTION

The present invention provides a method of moisturizing human skin comprising administering an effective amount of a microemulsion composition to skin in need of moisturizing, said composition comprising a specified moisturizing agent, as well as a microemulsion forming surfactant, a polysiloxane, and a skin humectant, and having an average droplet size in the range of about 0.001 microns to about 0.2 microns in diameter.

Another embodiment of this invention is a method of potentiating a macroemulsion moisturizing composition wherein a microemulsion composition is first applied to skin in need of moisturizing followed by application of a macroemulsion moisturizing composition. The microemulsion composition, used to potentiate the effects of a macroemulsion moisturizing composition, comprises a specified moisturizing agent, as well as a microemulsion forming surfactant, a polysiloxane, and a skin humectant, and has an average droplet size in the range of about 0.001 microns to about 0.2 microns in diameter.

Also provided by the present invention are new microemulsion compositions. More specifically, the invention provides water-in-oil microemulsion compositions comprising a specified moisturizing agent, as well as a microemulsion forming surfactant, a polysiloxane, and a skin humectant and having an average droplet size in the range of about 0.001 microns to about 0.2 microns in diameter.

Finally, the present invention provides a water-in-oil microemulsion composition comprising from about 1.0% by weight to about 8.0% by weight of a sunscreen; from about 15.0% by weight to about 79.0% by weight of a microemulsion forming surfactant, from about 15.0% by weight to about 79.0% by weight of a polysiloxane, and from about 5.0% by weight to about 50.0% by weight of a skin humectant and having an average droplet size in the range of about 0.001 microns to about 0.2 microns in diameter.

DETAILED DESCRIPTION OF THE INVENTION

Typically, one of the two immiscible liquids in an emulsion is aqueous while the other is an oil. Emulsions may be classified depending on which liquid forms the dispersed phase and which liquid forms the dispersoon medium. An emulsion in which oil is dispersed as droplets throughout the aqueous phase is termed an oil-in-water emulsion. When water is the dispersed phase and an oil is the dispersion medium, a water-in-oil emulsion exists. Whether the aqueous phase or the oil phase becomes the dispersed phase, or is the dispersion medium, depends primarily on the emulsifying agent used and the relative amounts of the two liquid phases. The emulsions contemplated for use in the methods of the present invention include both water-in-oil microemulsions, wherein the continuous phase is oil, and oil-in-water microemulsions, wherein the continuous phase is water. The preferred microemulsions contemplated for use in the instantly claimed methods are water-in-oil microemulsions.

As noted above, the present invention provides a method of moisturizing human skin comprising administering to skin in need of moisturizing an effective amount of a water-in-oil or oil-in-water microemulsion selected from the group consisting of one of the following compositions comprised of (a) from about 1.0% by weight to about 36.0% by weight of a fatty alcohol, from about 23.5% by weight to about 90.0% by weight of a microemulsion forming surfactant, from about 1.0% by weight to about 28.0% by weight of a polysiloxane, and from about 2.0% by weight to about 36.0% by weight of a skin humectant;

(b) from about 1.0% by weight to about 46.0% by weight of an animal oil, from about 14.0% by weight to about 90.0% by weight of a microemulsion forming surfactant, from about 1.0% by weight to about 35.0% by weight of a polysiloxane, and from about 2.0% by weight to about 18.0% by weight of a skin humectant;

(c) from about 1.0% by weight to about 31.0% by weight of a triglyceride, from about 37.0% by weight to about 90.0% by weight of a microemulsion forming surfactant, from about 1.0% by weight to about 35.0% by weight of a polysiloxane, and from about 2.0% by weight to about 24.0% by weight of a skin humectant;

(d) from about 1.0% by weight to about 41.0% by weight of a fatty diester, from about 23.0% by weight to about 90.0% by weight of a microemulsion forming surfactant, from about 1.0% by weight to about 31.0% by weight of a polysiloxane, and from about 2.0% by weight to about 42.0% by weight of a skin humectant;

(e) from about 1.0% by weight to about 41.0% by weight of a branched chain fatty ester, from about 18.5% by weight to about 90.0% by weight of a microemulsion forming surfactant, from about 1.0% by weight to about 31.0% by weight of a polysiloxane and from about 2.0% by weight to about 54.0% by weight of a skin humectant;

(f) from about 1.0% by weight to about 6.0% by weight of a fatty acid, from about 60.0% by weight to about 90.0% by weight of a microemulsion forming surfactant, from about 1.0% by weight to about 5.0% by weight of a polysiloxane, and from about 2.0% by weight to about 26.0% by weight of a skin humectant;

(g) from about 1.0% by weight to about 41.0% by weight of a tribasic acid ester, from about 23.0% by weight to about 90.0% by weight of a microemulsion forming surfactant, from about 1.0% by weight to about 31.0% by weight of a polysiloxane, and from about 3.0% by weight to about 33.0% by weight of a skin humectant;

(h) from about 3.0% by weight to about 35.0% by weight o a vegetable oil, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant;

(i) from about 5.0% by weight to about 35.0% by weight of a long chain hydrocarbon, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant; and (j) from about 5.0% by weight to about 35.0% by weight of a straight chain fatty ester, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant.

The present invention also provides a method of moisturizing human skin comprising administering to skin in need of moisturizing, first, an effective amount of a water-in-oil or oil-in-water microemulsion selected from the group consisting of one of the compositions discussed above, followed by subsequent application of a macroemulsion moisturizing composition.

Also encompassed within the present invention is a new water-in-oil microemulsion composition selected from the group consisting of one of the following compositions comprised of (a) from about 1.0% by weight to about 36.0% by weight of a fatty alcohol, from about 23.5% by weight to about 90.0% by weight of a microemulsion forming surfactant, from about 1.0% by weight to about 28.0% by weight of a polysiloxane, and from about 2.0% by weight to about 36.0% by weight of a skin humectant;

(b) from about 1.0% by weight to about 46.0% by weight of an animal oil, from about 14.0% by weight to about 90.0% by weight of a microemulsion forming surfactant, from about 1.0% by weight to about 35.0% by weight of a polysiloxane, and from about.2.0% by weight to about 18.0% by weight of a skin humectant;

(c) from about 1.0% by weight to about 31.0% by weight of a triglyceride, from about 37.0% by weight to about 90.0% by weight of a microemulsion forming surfactant, from about 1.0% by weight to about 35.0% by weight of a polysiloxane, and from about 2.0% by weight to about 24.0% by weight of a skin humectant;

(d) from about 1.0% by weight to about 41.0% by weight of a fatty diester, from about 23.0% by weight to about 90.0% by weight of a microemulsion forming surfactant, from about 1.0% by weight to about 31.0% by weight of a polysiloxane, and from about 2.0% by weight to about 42.0% by weight of a skin humectant;

(e) from about 5.0% by weight to about 35.0% by weight of a straight chain fatty ester, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant;

(f) from about 1.0% by weight to about 6.0% by weight of a fatty acid, from about 60.0% by weight to about 90.0% by weight of a microemulsion forming surfactant, from about 1.0% by weight to about 5.0% by weight of a polysiloxane, and from about 2.0% by weight to about 26.0% by weight of a skin humectant;

(g) from about 1.0% by weight to about 41.0% by weight of a tribasic acid ester, from about 23.0% by weight to about 90.0% by weight of a microemulsion forming surfactant, from about 1.0% by weight to about 31.0% by weight of a polysiloxane, and from about 3.0% by weight to about 33.0% by weight of a skin humectant;

(h) from about 3.0% by weight to about 35.0% by weight of a vegetable oil, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant;

(i) from about 5.0% by weight to about 35.0% by weight of a long chain hydrocarbon, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant; and (j) from about 1.0% by weight to about 41.0% by weight of a branched chain fatty ester, from about 18.5% by weight to about 90.0% by weight of a microemulsion forming surfactant, from about 1.0% by weight to about 31.0% by weight of a polysiloxane, and from about 2.0% by weight to about 54.0% by weight of a skin humectant.

Another water-in-oil microemulsion of the invention comprises from about 1.0% by weight to about 8.0% by weight of a sunscreen, from about 15.0% by weight to about 79.0% by weight of a microemulsion forming surfactant, from about 15.0% by weight to about 79.0% by weight of a polysiloxane, and from about 5.0% by weight to about 50.0% by weight of a skin humectant. The composition will preferably contain from about 2.0% by weight to about 6.0% by weight of a sunscreen, from about 20.0% by weight to about 35.0% by weight of a microemulsion forming surfactant, from about 20.0% by weight to about 55.0% by weight of a polysiloxane, and from about 20.0% by weight to about 35.0% by weight of a skin humectant.

The oil-in-water and water-in-oil microemulsions employed in the methods of the present invention, as well as the novel water-in-oil microemulsion compositions of the present invention, contain one or more ingredients which provide skin moisturizing microemulsions. These ingredients are selected from the group consisting of fatty alcohols, animal oils, triglycerides, fatty diesters, branched chain fatty esters, fatty acids, tribasic acid esters, vegetable oils, long chain hydrocarbons, and straight chain fatty esters.

Acceptable fatty alcohols useful in preparing the skin moisturizing microemulsions of the present invention contain one hydroxy group. Examples of acceptable fatty alcohols include behenyl alcohol, cetyl alcohol, isocetyl alcohol, isostearyl alcohol, lauryl alcohol, 2-octyldodecanol, oleyl alcohol, myristyl alcohol, and stearyl alcohol.

Acceptable animal oils include cod liver oil, lanolin oil, mink oil, orange roughy oil, and shark liver oil.

Typical triglycerides include caprylic/capric triglycerides, triisononanoin, triisostearin, trilaurin, trilinolein, and triolein.

Examples of fatty diesters include dibutyl adipate, dibutyl sebacate, dicetyl adipate, diethyl sebacate, dihexyl adipate, diisocetyl adipate, diisopropyl adipate, diisopropyl dimerate, diisopropyl sebacate, diisostearyl adipate, dioctyl adipate, dioctyl sebacate, and dioctyl succinate.

Acceptable branched chain fatty esters include 2-ethylhexyl isononanoate, 2-ethylhexyl myristate, 2-ethylhexyl oxystearate, 2-ethylhexyl palmitate, 2-ethylhexyl pelargonate, 2-ethylhexyl stearate, isocetyl isodecanoate, isocetyl palmitate, isodecyl isononanoate, isononyl isononanoate, isopropyl isostearate, isopropyl laurate, isopropyl linoleate, isopropyl myristate, isopropyl oleate, isopropyl palmitate, isopropyl stearate, isostearyl isostearate, isostearyl lactate, isostearyl neopentanoate, isostearyl palmitate, ispridecyl isononanoate, and tocopheryl linoleate.

Examples of acceptable fatty acids include isostearic acid, lauric acid, linoleic acid, linolenic acid, and oleic acid.

Typical tribasic acid esters include triisocetyl citrate, triisopropyl trilinoleate, triisostearyl trilinoleate, trilauryl citrate, and trioctyl citrate.

Acceptable vegatable oils include almond oil, apricot kernel oil, avocado oil, castor oil, coconut oil, corn oil, evening primrose oil, jojoba oil, olive oil, safflower oil, sesame oil, soybean oil, and wheat germ oil.

Examples of acceptable long chain hydrocarbons include squalane and squalene.

Acceptable straight chain fatty esters include lauryl lactate, lauryl myristate, lauryl palmitate, lauryl stearate, myristyl lactate, myristyl myristate, myristyl neopentanoate, myristyl propionate, myristyl stearate, oleyl erucate, oleyl linoleate, oleyl myristate, oleyl oleate, oleyl stearate, stearyl lactate, and stearyl oleate.

Preferred ingredients for use in the microemulsions employed in the present invention are fatty alcohols, such as isocetyl alcohol, cetyl alcohol, myristyl alcohol, and 2-octyldodecanol; animal oils, such as lanolin oil; triglycerides, such as caprylic/capric triglycerides; fatty diesters, such as diisopropyl sebacate and diisopropyl dimerate; branched chain fatty esters, such as isopropyl isostearate and isopropyl myristate; fatty acids, such as isostearic acid; and tribasic acid esters, such as triisocetyl citrate.

One or more sunscreens may be incorporated into the present microemulsions. A variety of sunscreens may be employed including the p-aminobenzoic acid derivatives such as p-(2-ethylhexyl)dimethylaminobenzoate, and benzophenone derivatives such as (2-hydroxy-4-methoxyphenyl)phenylmethanone. The exact amount of sunscreen employed in the present compositions will vary depending on the degree of protection desired from the sun's harmful rays.

The present composition may also contain both moisturizers and sunscreens in combination at concentrations similar to those described above when each ingredient is used alone.

A variety of microemulsion forming surfactants may be employed in the compositions of the invention. As used herein the term "microemulsion forming surfactant"is a surfactant selected from the group consisting of sorbitans, such as polysorbate 21 and polysorbate 60; poloxamers, such as Pluronic L-31; poloxamines, such as Tetronic 304; ethoxylated fatty alcohols, such as Brij; esters of phosphoric acid, such as PPG-10 cetyl ether phosphate and PPG-5 ceteth-10 phosphate; PEG castor oils, such as PEG-30 castor oil; polyoxyethylene alkylphenyl ethers, such s octoxynol-9 and nonoxynol-9; lanolin ethoxylates, such as PPG-20 lanolin ether and laneth-10 acetate; the sodium laureth sulfates; the glucose surfactants PPG-10 methyl glucose ether and PPG-20 methyl glucose ether; the sucrose ester sucrose ricinoleate; sodium lauryl sulfate; and sodium dodecyl sulfate. A preferred group of surfactants used in selecting a microemulsion forming surfactant are the sorbitans, the sodium laureth sulfates, sodium lauryl sulfate and sodium dodecyl sulfate.

A variety of polysiloxane compounds may be employed in the compositions of the invention. These polysiloxanes may be volatile or non-volatile and include the cyclic dimethyl polysiloxanes having from three to six silicon atoms, such as cyclomethicone, as well as linear polysiloxanes having a viscosity of ten centistokes, or less, at room temperature (25° C.), and mixtures thereof. A preferred polysiloxane employed in the compositions of the invention is cyclomethicone.

The compositions of the invention will also contain one or more suitable skin compatible humectants. These humectants are polar in nature and include deionized water, as well as polyhydric alcohols such as propylene glycol, glycerine, or sorbitol.

All cosmetic compositions must be protected against the growth of potentially harmful microorganisms, and therefore preservatives are added as a routine. While it is in the aqueous phase that microorganisms tend to grow, microorganisms can also reside in the oil phase. As such, preservatives which have solubility in both water and oil are preferably employed in the present compositions. Generally from one tenth of one percent by weight to one percent by weight of preservatives are adequate. The traditional preservatives for cosmetics and pharmaceuticals are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives for a preferred emulsion product of this invention are methyl and propyl para-hydroxybenzoates, imidazolidinyl urea, and quaternium-15. The preservatives should be selected having regard for the use of the composition and possible incompatibilities between the preservatives and the other ingredients in the emulsion.

The microemulsion compositions of the invention may also contain one or more pigments so as to provide coloration to the composition, and a fragrance, such as Firmenich and Co. 66.001/NY/G fragrance oil, to make the composition soothing to the olfactory system. The amount of these ingredients present in the composition will depend on the specific effect desired.

The compositions of the invention may be prepared by procedures well known to formulation chemists. Typically, an oil phase is prepared by combining all hydrophobic components, as well as the water-insoluble solids, in a container and heating the resulting mixture under agitation until all the ingredients are dissolved. In a separate container, an aqueous phase is prepared by combining all of the hydrophilic components, as well as the oil-insoluble solids, and heating the resulting mixture under constant stirring until the mixture is homogeneous. The microemulsion forming surfactant, or surfactants, are separately combined and mixed until homogeneous, and heat may be applied if necessary. The three phases thus prepared are combined and stirred until homogeneous and the solution becomes clear when allowed to stand at room temperature. The composition is finally allowed to stand for approximately 24 hours in order for the composition to achieve equilibrium. The composition may be transferred to appropriate containers for storage until needed for application to individuals in need of a microemulsion of the invention.

As noted above, the compositions of the invention are translucent, and typically transparent since the average droplet size of a microemulsion being very small compared to the macroemulsion average droplet size (from about 10 microns or more in diameter) will not reflect light. As such, the compositions of the invention will have a droplet size in the range of about 0.001 microns to about 0.2 micron in diameter, more typically in the range of about 0.001 microns to about 0.14 microns in diameter.

The compositions of the invention are useful for a variety of purposes, especially for protecting the skin's surface. Such protection may be from the sun, wind, or rain. The present microemulsions are particularly well suited for moisturizing skin and this is the primary use contemplated for the microemulsions. To assist in protecting skin from the sun, a sunscreen may be incorporated into the microemulsions of the invention.

In addition, the microemulsion compositions employed i.n the present invention provide superior results when applied to skin since they leave little residue on the surface of the skin following their application. Further, the compositions are generally not irritating to the skin when formulated with the proper balance of non-ionic surfactants.

It is important from a commercial standpoint that the compositions of the invention remain stable over a range of temperatures and under various conditions. For example, these compositions may be used under warm, humid conditions in the summer, or under cold, dry conditions in the winter. While such stability is important from an esthetic point of view, this generally does not substantially affect the operability of the microemulsions of the invention.

As noted above, the microemulsions specified herein are useful in moisturizing human skin. Therefore, one embodiment of the present invention is a method of moisturizing human skin comprising administering an effective amount of a microemulsion as specified herein to skin in need of moisturization.

The term "effective amount", as used herein, represents an amount of a microemulsion capable of moisturizing or preventing dry skin. The particular quantity of microemulsion administered according to this invention will, of course, be determined by the particular circumstances surrounding its use, including the microemulsion administered, the condition of the skin, the age of the user, the degree of moisturization desired, and similar considerations. The microemulsions are administered transdermally by application to the skin. Typically, a single application will be applied by the topical administration of a sufficient amount of a microemulsion to adequately cover the affected area of the skin. Subsequent applications may be made as needed in order to maintain the desired level of moisturization of the skin.

The microemulsions employed in the present invention are particularly important because of their ability to increase the rate of penetration of the moisturizing agents incorporated therein to the areas of skin in need of moisturization. Tests have been conducted in laboratory animals comparing microemulsions containing a radiolabeled ingredient with commercially available macroemulsion moisturizers. These tests have shown that greater amounts of the radiolabeled material reach the dermis and epidermis of the skin faster for the microemulsion moisturizer. Tests on laboratory animals have also indicated that the microemulsions employed in the present invention cause epidermal thickening. Epidermal thickening can lead to a highly desirable increase in skin resilience and elasticity.

It has also been discovered that the microemulsions employed in the invention have the ability to potentiate the effect of subsequently applied macroemulsion moisturizers. By first applying a microemulsion specified herein to the skin, ollowed by application of a macroemulsion moisturizing composition, the microemulsion has been shown to enhance the penetration of the subsequently applied moisturizing composition. Thus the rate of penetration of an individual's favorite macroemulsion moisturizing composition is increased as compared to the rate of penetration of that moisturizing composition alone. As such, the present invention provides as an additional embodiment a method of potentiating a macroemulsion moisturizing composition wherein a microemulsion is first applied to the skin followed by the application of a macroemulsion moisturizing composition.

Macroemulsion moisturizing compositions are well known in the art. As described previously a macroemulsion consists of an oil-in-water or water-in-oil emulsion wherein the average droplet size is from about 10 microns to about 1000 microns in diameter. Such emulsions exist in both lotion and cream form and are often opaque or white in appearance due to the larger droplet size. Macroemulsion moisturizing compositions encompassed within the presently disclosed potentiation method are emulsions of the above size which have a moisturizing effect. Illustrative of the types of macroemulsion moisturizing compositions included within the present invention are lotions, such as Elizabeth Arden's Advance Energizing Extract and Esté Lauder's Dramatically Different Moisturizing Lotion, and creams such as Elizabeth Arden's Visible Difference.

The following Examples illustrate formulations employed in the invention, and methods for their preparation. The Examples are not intended to be limiting to the scope of the present invention in any respect and should not be so construed.

EXAMPLE 1

An oil phase was prepared by combining 1000 g (25.0%) of Silicone 344 Fluid (cyclomethicone from Dow Corning Corp., Midland, Mich.), 788 g (19.7%) of Robane (squalane from Robeco Chemicals, Inc., New York, N.Y.), 80 g (2.0%) of Ritachol 1000 (non-ionic emulsifier from R.I.T.A. Chemicals Corp., Crystal Lake, Ill.), and 120 g (3.0%) of isopropyl myristate and stirring the resulting mixture under heat until homogeneous. To the oil phase was added 6 g (0.15%) of methylparaben and 6 g (0.15%) of propylparaben and the resulting mixture was heated, at about 50° C., until the two paraben derivatives were dissolved. In a separate container a water phase was prepared by dissolving 8 g (0.2%) of Germall 115 (imidazolidinyl urea from Sutton Laboratories, Inc., Chatham, N.J.) in a solution of 80 g (2.0%) of glycerine and 912 g (22.8%) of deionized water. The water and oil phases were combined. To the resulting mixture was added 1000 g (25.0%) of Tween 21 (polysorbate 21 from ICI Americas, Inc., Wilmington, Del.) at room temperature and the mixture was allowed to equilibrate overnight prior to transferring the resulting water-in-oil microemulsion composition into appropriate containers for storage.

EXAMPLE 2

A water-in-oil microemulsion composition of the invention containing the following ingredients was prepared according to the procedure of Example 1:

| Phase | Ingredient | Weight (g) | Weight % |
|---|---|---|---|
| Oil | Silcone 344 Fluid | 800 | 20.0 |
| | Robane | 588 | 14.7 |
| | Ritachol 1000 | 80 | 2.0 |
| | isopropyl myristate | 120 | 3.0 |
| | jojoba oil | 400 | 10.0 |
| Water | deionized water | 832 | 20.8 |
| | glycerine | 160 | 4.0 |
| | methylparaben | 6 | 0.15 |
| | propylparaben | 6 | 0.15 |
| | Germall 115 | 8 | 0.2 |
| Surfactant | T-Maz 21 (polysorbate 21 from Mazer Chemicals Inc., Gurnee, Illinois) | 1000 | 25.0 |

EXAMPLE 3

A water-in-oil microemulsion of the invention was prepared containing the following ingredients according to the general procedure of Example 1.

| Phase | Ingredient | Weight (g) | Weight % |
|---|---|---|---|
| Oil | Silcone 344 Fluid | 200 | 20.0 |
| | Robane | 129 | 12.9 |
| | jojoba oil | 100 | 10.0 |
| | isopropyl myristate | 30 | 3.0 |
| | propylparaben | 1 | 0.1 |
| | propylene glycol | 20 | 2.0 |
| | myristyl alcohol | 10 | 1.0 |
| | cetyl alcohol | 6 | 0.6 |
| | polysorbate 60 | 4 | 0.4 |
| Water | deionized water | 244 | 24.4 |
| | Germall 115 | 3 | 0.3 |
| | methylparaben | 3 | 0.3 |
| Surfactant | polysorbate 21 | 250 | 25.0 |

EXAMPLE 4

Following the procedure outlined in Example 3, the following ingredients were formulated to provide a water-in-oil microemulsion of the invention.

| Phase | Ingredient | Weight (g) | Weight % |
|---|---|---|---|
| Oil | Silcone 344 Fluid | 800 | 20.0 |
| | Robane | 594 | 14.85 |
| | isopropyl myristate | 120 | 3.0 |
| | jojoba oil | 400 | 10.0 |
| Water | glycerine | 80 | 2.0 |
| | deionized water | 904 | 22.6 |
| | propylparaben | 6 | 0.15 |
| | methylparaben | 6 | 0.15 |
| | Germall 115 | 8 | 0.20 |
| Surfactant | sodium dodecyl sulfate | 2 | 0.05 |
| | T-Maz 21 | 1080 | 27.0 |

EXAMPLE 5

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 24.22 | 24.22 |
| | isocetyl alcohol | 31.98 | 31.98 |
| | propyl paraben | 0.1 | 0.1 |
| Water | deionized water | 16.98 | 16.98 |
| | propylene glycol | 1.41 | 1.41 |
| | Dowicil 200 (quaternium-15) | 0.2 | 0.2 |
| | methyl paraben | 0.1 | 0.1 |
| Surfactant | polysorbate 21 | 23.15 | 23.15 |
| | polysorbate 60 | 0.37 | 0.37 |
| | myristyl alcohol | 0.93 | 0.93 |
| | cetyl alcohol | 0.56 | 0.56 |

EXAMPLE 6

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 15.09 | 15.09 |
| | lanolin oil | 19.92 | 19.92 |
| | propyl paraben | 0.10 | 0.10 |
| Water | deionized water | 13.45 | 13.45 |
| | propylene glycol | 1.13 | 1.13 |
| | Dowicil 200 | 0.20 | 0.20 |
| | methyl paraben | 0.10 | 0.10 |
| Surfactant | polysorbate 21 | 46.30 | 46.30 |
| | polysorbate 60 | 0.74 | 0.74 |
| | myristyl alcohol | 1.85 | 1.85 |
| | cetyl alcohol | 1.12 | 1.12 |

EXAMPLE 7

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 18.96 | 18.96 |
|  | caprylic/capric triglyceride | 25.04 | 25.04 |
|  | propyl paraben | 0.10 | 0.10 |
| Water | deionized water | 9.76 | 9.76 |
|  | propylene glycol | 0.83 | 0.83 |
|  | Dowicil 200 | 0.20 | 0.20 |
|  | methyl paraben | 0.10 | 0.10 |
| Surfactant | polysorbate 21 | 41.67 | 41.67 |
|  | polysorbate 60 | 0.67 | 0.67 |
|  | myristyl alcohol | 1.67 | 1.67 |
|  | cetyl alcohol | 1.00 | 1.00 |

EXAMPLE 8

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 21.12 | 21.12 |
|  | diisopropyl sebacate | 27.88 | 27.88 |
|  | propyl paraben | 0.10 | 0.10 |
| Water | deionized water | 19.02 | 19.02 |
|  | propylene glycol | 1.58 | 1.58 |
|  | Dowicil 200 | 0.20 | 0.20 |
|  | methyl paraben | 0.10 | 0.10 |
| Surfactant | polysorbate 21 | 27.78 | 27.78 |
|  | polysorbate 60 | 0.44 | 0.44 |
|  | myristyl alcohol | 1.11 | 1.11 |
|  | cetyl alcohol | 0.67 | 0.67 |

EXAMPLE 9

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 17.76 | 17.76 |
|  | isopropyl isostearate | 23.44 | 23.44 |
|  | propyl paraben | 0.10 | 0.10 |
| Water | deionized water | 30.85 | 30.85 |
|  | propylene glycol | 2.54 | 2.54 |
|  | Dowicil 200 | 0.20 | 0.20 |
|  | methyl paraben | 0.10 | 0.10 |
| Surfactant | polysorbate 21 | 23.15 | 23.15 |
|  | polysorbate 60 | 0.37 | 0.37 |
|  | myristyl alcohol | 0.93 | 0.93 |
|  | cetyl alcohol | 0.56 | 0.56 |

EXAMPLE 10

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 4.56 | 4.56 |
|  | isostearic acid | 6.02 | 6.02 |
|  | propyl paraben | 0.10 | 0.10 |
| Water | deionized water | 17.7 | 17.7 |
|  | propylene glycol | 1.47 | 1.47 |
|  | Dowicil 200 | 0.20 | 0.20 |
|  | methyl paraben | 0.10 | 0.10 |
| Surfactant | polysorbate 21 | 64.68 | 64.68 |
|  | polysorbate 60 | 1.03 | 1.03 |
|  | myristyl alcohol | 2.58 | 2.58 |
|  | cetyl alcohol | 1.56 | 1.56 |

EXAMPLE 11

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 21.12 | 21.12 |
|  | triisocetyl citrate | 27.88 | 27.88 |
|  | propyl paraben | 0.10 | 0.10 |
| Water | deionized water | 19.02 | 19.02 |
|  | propylene glycol | 1.58 | 1.58 |
|  | Dowicil 200 | 0.10 | 0.10 |
|  | methyl paraben | 0.20 | 0.20 |
| Surfactant | polysorbate 21 | 27.78 | 27.78 |
|  | polysorbate 60 | 0.44 | 0.44 |
|  | myristyl alcohol | 1.11 | 1.11 |
|  | cetyl alcohol | 0.67 | 0.67 |

EXAMPLE 12

A water-in-oil microemulsion composition of the invention containing the following ingredients was prepared according to the procedure of Example 1:

| Phase | Ingredient | Weight (g) | Weight % |
|---|---|---|---|
| Oil | cyclomethicone | 21.03 | 21.03 |
|  | diisopropyl dimerate | 27.77 | 27.77 |
|  | propyl paraben | 0.10 | 0.10 |
| Water | deionized water | 23.82 | 23.82 |
|  | propylene glycol | 1.97 | 1.97 |
|  | Dowicil 200 | 0.20 | 0.20 |
|  | methyl paraben | 0.10 | 0.10 |
| Surfactant | polysorbate 21 | 23.15 | 23.15 |
|  | polysorbate 60 | 0.37 | 0.37 |
|  | myristyl alcohol | 0.93 | 0.93 |
|  | cetyl alcohol | 0.56 | 0.56 |

EXAMPLE 13

An oil phase was prepared by combining 0.49 g (0.49%) of cetyl alcohol, 0.81 g (0.81%) of myristyl alcohol, 0.15 g (0.15%) of methylparaben, 0.15 g (0.15%) of propylparaben, 0.32 g (0.32%) of polysorbate 60, 2.17 g (2.17%) of isocetyl alcohol, and 2.17 g (2.17%) of 2-octyldodecanol, and heating the resulting mixture with agitation until all solids had dissolved. The remainder of the oil phase ingredients were added; 25.93 g (25.93%) cyclomethicone, 12.08 g (12.08%) squalane, 3.12 g (3.12%) jojoba oil, 3.12 g (3.12%) isopropyl myristate, 3.12 g (3.12%) p-(2-ethylhexyl)dimethylaminobenzoate, and the mixture stirred until homogeneous. To the oil phase was added 21.66 g (21.66%) polysorbate 21 and 0.25 g (0.25%) fragrance oil and the resulting mixture stirred until homogeneous. A water phase was prepared in a separate container by combining 18.79 g (18.79%) deionized water, 0.20 g (0.20%) Dowicil 200, 0.22 g (0.22%) sodium lauryl sulfate, 0.83 g (0.83%) butylene glycol, 1.00 g (1.00%) 2-phenoxyethanol, 1.25 g (1.25%) propylene glycol, and 2.17 g (2.17%) sodium laureth sulfate (30% by weight in water), and heating the resulting mixture under agitation until homogeneous. The water phase was added to the previously prepared mixture and the resulting composition stirred until homogeneous. Once the mixture was homogeneous the composition was stored at room temperature until ready for use.

Two water-in-oil microemulsions of the invention were prepared containing a sunscreen. The preparation of these compositions is illustrated below.

EXAMPLE 14

An oil phase was prepared by combining 260 g (26.0%) of Silicone 344 Fluid, 157 g (15.7%) of Robane, 30 g (3.0%) of isopropyl myristate, 30 g (3.0%) of Escalol 507 (p-(2-ethylhexyl)dimethylaminobenzoate) and 20 g (2.0%) of (2-hydroxy-4-methoxyphenyl)phenylmethanone, and heating the resulting mixture with agitation until homogeneous. To the oil phase was added 1.5 g (0.15%) of propylparaben, and the resulting mixture was stirred until the propylparaben was dissolved. A water phase was prepared in a separate container by combining 248 ml (24.8%) of water and 1.5 g (0.15%) of methylparaben with 2.0 g (0.2%) of Germall 115 and heating the resulting mixture under agitation until homogeneous. The oil and water phases were combined and 250 g (25.0%) of T-Maz 21 was added thereto. The resulting composition was stirred until homogeneous and stored at room temperature until ready for use.

EXAMPLE 15

An oil phase was prepared by combining 1040 g (26.0%) of Silicone 344 Fluid, 628 g (15.7%) of Robane, 120 g (3.0%) of isopropyl myristate, 120 g (3.0%) of Escalol 507 and 80 g (2.0%) of (2-hydroxy-4-methoxyphenyl)phenylmethanone in a suitable container. The mixture was heated and stirred until homogeneous. To the oil phase was added 6 g (0.15%) of methylparaben and 6 g (0.15%) of propylparaben with stirring until the mixture was homogeneous. A water phase was prepared in a separate container by combining 992 g (24.8%) of water with 8 g (0.2%) of Germall 115 and 8 g (0.2%) of sodium dodecyl sulfate. The oil and water phases were combined and 992 g (24.8%) of Tween 21 was added thereto. The mixture was stirred until homogeneous and stored at room temperature until ready for use.

Certain of the compositions of the invention were tested to demonstrate efficacy as moisturizing agents. The test was conducted on dry skin, and the compositions to be tested were used over a 3-week period, followed by a two-week regression period. Thirty-two subjects were used in the study to test the efficacy of the formulations. Subjects were divided into two groups of 16 and each member of one group randomly received the formulation of Example 1 on one leg and the formulation of Example 2 on the other leg. In the second group subjects randomly received the formulation of Example 4 on one leg. The study was carried out for seven weeks. For the first two weeks, skin was allowed to dry. For the next three weeks treatment was conducted, and the final two weeks were a regression period. Subjects with obvious skin conditions, extensive varicose veins, deep suntans, or conditions on their legs other than dry skin were excluded from the study. Subjects ranged in age from 18 to 45 years. Evaluations were performed blind by the same evaluator, when possible. Evaluations were done 7, 5 and 3 days before application, the initial day of treatment prior to application, and 1, 2, 3, 4, 7, 9, 10, 11, 15, 16, 17, 18, 21, 22, 23, 24, 25, 28, 30, 32 and 35 days after the initial application. Test formulations were applied to the leg(s) twice each day for three weeks, once in the morning in the laboratory and each evening at home on weekdays. All weekend applications (morning and evening) were performed at home. No other skin moisturizers except the test formulations were allowed during the course of the study. In addition, the subjects were not allowed to swim or sunbathe. Showers, baths, and water contact to the legs were also not allowed the mornings that evaluations were performed.

Evaluations were performed according to the following scale:

0 = smooth, no evidence of dryness
1 = slightly dry skin
2 = moderately dry skin; peeling
3 = severely dry skin; flaking, peeling
4 = extremely dry skin; flaking, peeling and/or fissures Results (mean dryness scores) of each of the formulations were compared to the untreated control and to the positive control groups. In addition, each product was evaluated for significant change from day 0 for each evaluation day in the study. This data is presented below in Table I as the average of the 16 subjects employed.

TABLE I

| Days After First Application | Moisturization Study Formulation of Example No. | | |
|---|---|---|---|
|  | 1 | 2 | 4 |
| 0 | 3.0 | 3.0 | 3.0 |
| 1 | 2.0 | 1.8 | 2.3 |
| 2 | 0.9 | 0.8 | 1.3 |
| 3 | 0.3 | 0.4 | 0.8 |
| 4 | 0.5 | 0.3 | 0.6 |
| 7 | 0.1 | 0.1 | 0.7 |
| 9 | 0.5 | 0.4 | 0.4 |
| 10 | 0.3 | 0.2 | 0.5 |
| 11 | 0.1 | 0 | 0.5 |
| 15 | 0.9 | 0.7 | 1.3 |
| 16 | 0.2 | 0.2 | 0.8 |
| 17 | 0.2 | 0.3 | 0.4 |
| 18 | 0.1 | 0.1 | 0.3 |
| 21 | 0.1 | 0.1 | 0.3 |
| 22 | 0.5 | 0.3 | 0.9 |
| 23 | 0.2 | 0.3 | 1.3 |
| 24 | 0.5 | 0.3 | 1.1 |
| 25 | 0.5 | 0.4 | 1.1 |
| 28 | 0.9 | 0.6 | 1.6 |
| 30 | 1.1 | 1.0 | 1.9 |
| 32 | 1.8 | 1.8 | 2.3 |
| 35 | 2.4 | 2.4 | 2.8 |

The data generated from the preceding experiment indicate the effectiveness of the formulae of Examples 1 and 2 as moisturizers. The formula of Example 4 demonstrated moderate effectiveness as a moisturizer.

An additional moisturization study was conducted on the formulae of Examples 1 and 2. However, this data has not been supplied. Unusual and aberrant weather conditions which occurred during the test made interpretation of the results difficult.

We claim:

1. A method of moisturizing human skin comprising administering to skin in need of moisturizing an effective amount of a stable water-in-oil or oil-in-water microemulsion non-irritating moisturizing composition which when applied to skin promotes the penetration of moisturizers into the skin and leaves little residue on the surface of the skin following its application selected from the group consisting of one of the following compositions comprised of (a) from about 1.0% by weight to about 36.0% by weight of a fatty alcohol, from about 23.5% by weight to about 90.0% by weight of a microemulsion forming surfactant, from about 1.0% by weight to about 28.0% by weight of a polysiloxane, and from about 2.0% by weight to about 36.0% by weight of a skin humectant;

(b) from about 1.0% by weight to about 46.0% by weight of an animal oil, from about 14.0% by weight to about 90.0% by weight of a microemulsion forming surfactant, from about 1.0% by weight to about 35.0% by weight of a polysiloxane, and from about 2.0% by weight to about 18.0% by weight of a skin humectant;

(c) from about 1.0% by weight to about 31.0% by weight of a triglyceride, from about 37.0% by weight to about 90.0% by weight of a microemulsion forming surfactant, from about 1.0% by weight to about 35.0% by weight of a polysiloxane, and from about 2.0% by weight to about 24.0% by weight of a skin humectant;

(d) from about 1.0% by weight to about 41.0% by weight of a fatty diester, from about 23.0% by weight to about 90.0% by weight of a microemulsion forming surfactant, from about 1.0% by weight to about 31.0% by weight of a polysiloxane, and from about 2.0% by weight to about 42.0% by weight of a skin humectant;

(e) from about 1.0% by weight to about 41.0% by weight of a branched chain fatty ester, from about 18.5% by weight to about 90.0% by weight of a microemulsion forming surfactant, from about 1.0% by weight to about 31.0% by weight of a polysiloxane, and from about 2.0% by weight to about 54.0% by weight of a skin humectant;

(f) from about 1.0% by weight to about 6.0% by weight of a fatty acid, from about 60.0% by weight to about 90.0% by weight of a microemulsion forming surfactant, from about 1.0% by weight to about 5.0% by weight of a polysiloxane, and from about 2.0% by weight to about 26.0% by weight of a skin humectant;

(g) from about 1.0% by weight to about 41.0% by weight of a tribasic acid ester, from about 23.0% by weight to about 90.0% by weight of a microemulsion forming surfactant, from about 1.0% by weight to about 31.0% by weight of a polysiloxane, and from about 3.0% by weight to about 33.0% by weight of a skin humectant;

(h) from about 3.0% by weight to about 35.0% by weight of a vegetable oil, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant;

(i) from about 5.0% by weight to about 35.0% by weight of a long chain hydrocarbon, from about 20.0% by weight to about 80.0% by weight of a microemulsion forming surfactant, from about 10.0% by weight to about 70.0% by weight of a polysiloxane, and from abbut 5.0% by weight to about 50.0% by weight of a skin humectant; and (j) from about 5.0% by weight to about 35.0% by weight of a straight chain fatty ester, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant and the composition having an average droplet size in the range of about 0.001 microns to about 0.2 microns in diameter, and wherein the composition is adapted to promote the penetration of the moisturizers into the skin.

2. A method of claim 1 wherein the water-in-oil or oil-in-water microemulsion contains a fatty alcohol.

3. The method of claim 2 wherein the fatty alcohol is isocetyl alcohol.

4. A method of claim 1 wherein the water-in-oil or oil-in-water microemulsion contains an animal oil.

5. The method of claim 4 wherein the animal oil is lanolin oil.

6. A method of claim 1 wherein the water-in-oil or oil-in-water microemulsion contains a triglyceride.

7. The method of claim 6 wherein the triglyceride is caprylic/capric triglyceride.

8. A method of claim 1 wherein the water-in-oil or oil-in-water microemulsion contains a fatty diester.

9. The method of claim 8 wherein the fatty diester is diisopropyl sebacate.

10. The method of claim 8 wherein the fatty diester is diisopoopyl dimerate.

11. A method of claim 1 wherein the water-in-oil or oil-in-water microemulsion contains a branched chain fatty ester.

12. The method of claim 11 wherein the branched chain fatty ester is isopropyl isostearate.

13. The method of claim 11 wherein the branched chain fatty ester is isopropyl myristate.

14. The method of claim 13 wherein the microemulsion composition consists essentially of:

| Ingredient | Weight % |
| --- | --- |
| cyclomethicone | 25.93 |
| p-(2-ethylhexyl)-dimethylamino-benzoate | 3.12 |
| fragrance oil | 0.25 |
| squalane | 12.08 |
| jojoba oil | 3.12 |
| isopropyl myristate | 3.12 |
| myristyl alcohol | 0.81 |
| cetyl alcohol | 0.49 |
| isocetyl alcohol | 2.17 |
| 2-octyldodecanol | 2.17 |
| deionized water | 18.79 |
| propylene glycol | 1.25 |
| butylene glycol | 0.83 |
| polysorbate 21 | 21.66 |
| polysorbate 60 | 0.32 |
| sodium laureth sulfate (30% by weight in water) | 2.17 |
| sodium lauryl sulfate | 0.22 |
| 2-phenoxyethanol | 1.00 |
| quaternium-15 | 0.20 |
| methyl paraben | 0.15 |
| propyl paraben | 0.15 |

15. A method of claim 1 wherein the water-in-oil or oil-in-water microemulsion contains a fatty acid.

16. The method of claim 15 wherein the fatty acid is isostearic acid.

17. A method of claim 1 wherein the water-in-oil or oil-in-water microemulsion contains a tribasic acid ester.

18. The method of claim 17 wherein the tribasic acid ester is triisocetyl citrate.

19. A method of claim 1 wherein the water-in-oil or oil-in-water microemulsion contains a vegetable oil.

20. The method of claim 19 wherein the vegetable oil is jojoba oil.

21. A method of claim 1 wherein the water-in-oil or oil-in-water microemulsion contains a long chain hydrocarbon.

22. The method of claim 21 wherein the long chain hydrocarbon is squalane.

23. A method of claim 1 wherein the water-in-oil or oil-in-water microemulsion contains a straight chain fatty ester.

24. A method of claim 1 comprising the subsequent application of a macroemulsion moisturizing composition.

25. A method of claim 2 wherein a macroemulsion moisturizing composition is subsequently applied.

26. The method of claim 3 wherein a macroemulsion moisturizing composition is subsequently applied.

27. A method of claim 4 wherein a macroemulsion moisturizing composition is subsequently applied.

28. The method of claim 5 wherein a macroemulsion moisturizing composition is subsequently applied.

29. A method of claim 6 wherein a macroemulsion moisturizing composition is subsequently applied.

30. The method of claim 7 wherein a macroemulsion moisturizing composition is subsequently applied.

31. A method of claim 8 wherein a macroemulsion moisturizing composition is subsequently applied.

32. The method of claim 9 wherein a macroemulsion moisturizing composition is subsequently applied.

33. The method of claim 10 wherein a macroemulsion moisturizing composition is subsequently applied.

34. A method of claim 11 wherein a macroemulsion moisturizing composition is subsequently applied.

35. The method of claim 12 wherein a macroemulsion moisturizing composition is subsequently applied.

36. A method of claim 13 wherein a macroemulsion moisturizing composition is subsequently applied.

37. The method of claim 14 wherein a macroemulsion moisturizing composition is subsequently applied.

38. A method of claim 15 wherein a macroemulsion moisturizing composition is subsequently applied.

39. The method of claim 16 wherein a macroemulsion moisturizing composition is subsequently applied.

40. A method of claim 17 wherein a macroemulsion moisturizing composition is subsequently applied.

41. The method of claim 18 wherein a macroemulsion moisturizing composition is subsequently applied.

42. A method of claim 19 wherein a macroemulsion moisturizing composition is subsequently applied.

43. The method of claim 20 wherein a macroemulsion moisturizing composition is subsequently applied.

44. A method of claim 21 wherein a macroemulsion moisturizing composition is subsequently applied.

45. The method of claim 22 wherein a macroemulsion moisturizing composition is subsequently applied.

46. The method of claim 23 wherein a macroemulsion moisturizing composition is subsequently applied.

47. A stable water-in-oil microemulsion non-irritating moisturizing composition which when applied to skin promotes the penetration of moisturizers into the skin and leaves little residue on the surface of the skin following its application composition selected from the group consisting of one of the following compositions comprised of (a) from about 1.0% by weight to about 36.0% by weight of a fatty alcohol, from about 23.5% by weight to about 90.0% by weight of a microemulsion forming surfactant, from about 1.0% by weight to about 28.0% by weight of a polysiloxane, and from about 2.0% by weight to about 36.0% by weight of a skin humectant;

(b) from about 1.0% by weight to about 46.0% by weight of an animal oil, from about 14.0% by weight to about 90.0% by weight of a microemulsion forming surfactant, from about 1.0% by weight to about 35.0% by weight of a polysiloxane, and from about 2.0% by weight to about 18.0% by weight of a skin humectant;

(c) from about 1.0% by weight to about 31.0% by weight of a triglyceride, from about 37.0% by weight to about 90.0% by weight of a microemulsion forming surfactant, from about 1.0% by weight to about 35.0% by weight of a polysiloxane, and from about 2.0% by weight to about 24.0% by weight of a skin humectant;

(d) from about 1.0% by weight to about 41.0% by weight of a fatty diester, from about 23.0% by weight to about 90.0% by weight of a microemulsion forming surfactant, from about 1.0% by weight to about 31.0% by weight of a polysiloxane, and from about 2.0% by weight to about 42.0% by weight of a skin humectant;

(e) from about 5.0% by weight to about 35.0% by weight of a straight chain fatty ester, from about 20.0% by weight to about 80.0% by weight of a microemulsion forming surfactant, from about 10.0% by weight to about 70.0% by weight of a polysiloxane, and from about 5.0% by weight to about 50.0% by weight of a skin humectant;

(f) from about 1.0% by weight to about 6.0% by weight of a fatty acid, from about 60.0% by weight to about 90.0% by weight of a microemulsion forming surfactant, from about 1.0% by weight to about 5.0% by weight of a polysiloxane, and from about 2.0% by weight to about 26.0% by weight of a skin humectant; and (g) from about 1.0% by weight to about 41.0% by weight of a tribasic acid ester, from about 23.0% by weight to about 90.0% by weight of a microemulsion forming surfactant, from about 1.0% by weight to about by weight of a polysiloxane, and from about 3.0% by weight to about 33.0% by weight of a skin humectant and the composition having an average droplet size in the range of about 0.001 microns to about 0.2 microns in diameter, and wherein the composition is adapted to promote the penetration of the moisturizers into the skin.

48. The compositions of claim 47 comprising as additional ingredients from about 0.1% by weight to about 1.0% by weight of preservatives.

49. The composition of claim 48 consisting essentially of the following ingredients:

| Ingredient | Weight % |
| --- | --- |
| cyclomethicone | 24.22 |
| isocetyl alcohol | 31.98 |
| myristyl alcohol | 0.93 |
| cetyl alcohol | 0.56 |

-continued

| Ingredient | Weight % |
| --- | --- |
| deionized water | 16.98 |
| propylene glycol | 1.41 |
| polysorbate 21 | 23.15 |
| polysorbate 60 | 0.37 |
| propyl paraben | 0.1 |
| quaternium-15 | 0.2 |
| methyl paraben | 0.1 |

50. The composition of claim 48 consisting essentially of the following ingredients:

| Ingredient | Weight % |
| --- | --- |
| cyclomethicone | 15.09 |
| lanolin oil | 19.92 |
| myristyl alcohol | 1.85 |
| cetyl alcohol | 1.12 |
| deionized water | 13.45 |
| propylene glycol | 1.13 |
| polysorbate 21 | 46.30 |
| polysorbate 60 | 0.74 |
| propyl paraben | 0.10 |
| quaternium-15 | 0.20 |
| methyl paraben | 0.10 |

51. The composition of claim 48 consisting essentially of the following ingredients:

| Ingredient | Weight % |
| --- | --- |
| cyclomethicone | 18.96 |
| caprylic/capric triglyceride | 25.04 |
| myristyl alcohol | 1.67 |
| cetyl alcohol | 1.00 |
| deionized water | 9.76 |
| propylene glycol | 0.83 |
| polysorbate 21 | 41.67 |
| polysorbate 60 | 0.67 |
| propyl paraben | 0.10 |
| quaternium-15 | 0.20 |
| methyl paraben | 0.10 |

52. The composition of claim 48 consisting essentially of the following ingredients:

| Ingredient | Weight % |
| --- | --- |
| cyclomethicone | 21.12 |
| diisopropyl sebacate | 27.88 |
| myristyl alcohol | 1.11 |
| cetyl alcohol | 0.67 |
| deionized water | 19.02 |
| propylene glycol | 1.58 |
| polysorbate 21 | 27.78 |
| polysorbate 60 | 0.44 |
| propyl paraben | 0.10 |
| quaternium-15 | 0.20 |
| methyl paraben | 0.10 |

53. The composition of claim 48 consisting essentially of the following ingredients:

| Ingredient | Weight % |
| --- | --- |
| cyclomethicone | 17.76 |
| isopropyl isostearate | 23.44 |
| myristyl alcohol | 0.93 |
| cetyl alcohol | 0.56 |
| deionized water | 30.85 |
| propylene glycol | 2.54 |
| polysorbate 21 | 23.15 |
| polysorbate 60 | 0.37 |

-continued

| Ingredient | Weight % |
| --- | --- |
| propyl paraben | 0.10 |
| quaternium-15 | 0.20 |
| methyl paraben | 0.10 |

54. The composition of claim 48 consisting essentially of the following ingredients:

| Ingredient | Weight % |
| --- | --- |
| cyclomethicone | 4.56 |
| isostearic acid | 6.02 |
| myristyl alcohol | 2.58 |
| cetyl alcohol | 1.56 |
| deionized water | 17.7 |
| propylene glycol | 1.47 |
| polysorbate 21 | 64.68 |
| polysorbate 60 | 1.03 |
| propyl paraben | 0.10 |
| quaternium-15 | 0.20 |
| methyl paraben | 0.10 |

55. The composition of claim 48 consisting essentially of the following ingredients:

| Ingredient | Weight % |
| --- | --- |
| cyclomethicone | 21.12 |
| triisocetyl citrate | 27.88 |
| myristyl alcohol | 1.11 |
| cetyl alcohol | 0.67 |
| deionized water | 19.02 |
| propylene glycol | 1.58 |
| polysorbate 21 | 27.78 |
| polysorbate 60 | 0.44 |
| propyl paraben | 0.10 |
| quaternium-15 | 0.10 |
| methyl paraben | 0.20 |

56. The composition of claim 48 consisting essentially of the following ingredients:

| Ingredient | Weight % |
| --- | --- |
| cyclomethicone | 21.03 |
| diisopropyl dimerate | 27.77 |
| myristyl alcohol | 0.93 |
| cetyl alcohol | 0.56 |
| deionized water | 23.82 |
| propylene glycol | 1.97 |
| polysorbate 21 | 23.15 |
| polysorbate 60 | 0.37 |
| propyl paraben | 0.10 |
| quaternium-15 | 0.20 |
| methyl paraben | 0.10 |

57. The composition of claim 48 consisting essentially of the following ingredients:

| Ingredient | Weight % |
| --- | --- |
| cyclomethicone | 25.93 |
| p-(2-ethylhexyl)-dimethylamino-benzoate | 3.12 |
| fragrance oil | 0.25 |
| squalane | 12.08 |
| jojoba oil | 3.12 |
| isopropyl myristate | 3.12 |
| myristyl alcohol | 0.81 |
| cetyl alcohol | 0.49 |
| isocetyl alcohol | 2.17 |
| 2-octyldodecanol | 2.17 |
| deionized water | 18.79 |

-continued

| Ingredient | Weight % |
|---|---|
| propylene glycol | 1.25 |
| butylene glycol | 0.83 |
| polysorbate 21 | 21.66 |
| polysorbate 60 | 0.32 |
| sodium laureth sulfate | 2.17 |

-continued

| Ingredient | Weight % |
|---|---|
| (30% by weight in water) | |
| sodium lauryl sulfate | 0.22 |
| 2-phenoxyethanol | 1.00 |
| quaternium-15 | 0.20 |
| methyl paraben | 0.15 |
| propyl paraben | 0.15 |

* * * * *

UNITED STATES PATENT AND TRADEMARK OFFICE
CERTIFICATE OF CORRECTION

PATENT NO. : 4,797,273

DATED : January 10, 1989

INVENTOR(S) : Linn, et al.

It is certified that error appears in the above-identified patent and that said Letters Patent is hereby corrected as shown below:

Column 3, line 29, delete "o" and insert --of--.

Column 5, line 39, delete "isopridecyl" and insert --isotridecyl--.

Column 7, line 51, delete "i.n" and insert --in--.

Column 8, line 40, delete "ollowed" and insert --followed--.

Column 16, line 29, delete "diisopoopyl" and insert --diisopropyl--.

Column 18, line 51, delete "about by" and insert --about 31.0% by--.

Signed and Sealed this

Twenty-first Day of November, 1989

Attest:

JEFFREY M. SAMUELS

*Attesting Officer*   *Acting Commissioner of Patents and Trademarks*